(12) United States Patent
Bai et al.

(10) Patent No.: US 10,993,103 B2
(45) Date of Patent: Apr. 27, 2021

(54) USING TIME-OF-FLIGHT TO DETECT AND CORRECT MISALIGNMENT IN PET/CT IMAGING

(71) Applicant: KONINKLIJKE PHILIPS N.V., Eindhoven (NL)

(72) Inventors: Chuanyong Bai, Solon, OH (US); Andriy Andreyev, Willoughby Hills, OH (US); Bin Zhang, Cleveland, OH (US); Xiyun Song, Cupertino, CA (US); Jinghan Ye, Livermore, CA (US); Zhiqiang Hu, Twinsburg, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 138 days.

(21) Appl. No.: 16/474,113

(22) PCT Filed: Jan. 2, 2018

(86) PCT No.: PCT/EP2018/050013
§ 371 (c)(1),
(2) Date: Jun. 27, 2019

(87) PCT Pub. No.: WO2018/127470
PCT Pub. Date: Jul. 12, 2018

(65) Prior Publication Data
US 2019/0355159 A1    Nov. 21, 2019

Related U.S. Application Data
(60) Provisional application No. 62/433,013, filed on Dec. 12, 2016.

(51) Int. Cl.
*G06T 7/00* (2017.01)
*G06T 11/00* (2006.01)
(Continued)

(52) U.S. Cl.
CPC .............. *H04W 8/14* (2013.01); *G06T 7/0016* (2013.01); *G06T 7/13* (2017.01); *G06T 11/005* (2013.01);
(Continued)

(58) Field of Classification Search
USPC .................................................. 382/128, 131
See application file for complete search history.

(56) References Cited

U.S. PATENT DOCUMENTS 8,000,513 B2 * 8/2011 Defrise ................. G06T 11/006
382/132
8,457,380 B2 * 6/2013 Wang .................... G06T 11/006
382/131
(Continued)

FOREIGN PATENT DOCUMENTS

CN      106491153 A    3/2017
WO    2008146186 A2   12/2008

OTHER PUBLICATIONS

Maurizio Conti, Why is TOF PET reconstruction a more robust method in the presence of inconsistent data?, 2010, Institute of Physics and Engineering in Medicine, 0031-9155/11/010155, pp. 155-168. (Year: 2010).*
(Continued)

*Primary Examiner* — Ishrat I Sherali (57) ABSTRACT

In positron emission tomography (PET) imaging, PET imaging data (22) having TOF localization is reconstructed. TOF image reconstruction (30) is performed on the PET imaging data to produce a TOF reconstructed image (32). The TOF image reconstruction utilizes the TOF localization of the PET imaging data. Non-TOF image reconstruction (40) is also performed on the PET imaging data to produce a non-TOF reconstructed image (42). The non-TOF image reconstruction does not utilize the TOF localization of the PET imaging data. A comparison image (50) is computed
(Continued)

which is indicative of differences between the TOF reconstructed image and the non TOF reconstructed image. An adjustment (54) is determined for the TOF image reconstruction based on the comparison image, such as alignment correction of an attenuation map (18), and the TOF image reconstruction is repeated on the PET imaging data with the determined adjustment to produce an adjusted TOF reconstructed image.

20 Claims, 6 Drawing Sheets

(51) Int. Cl.
| | | |
|---|---|---|
| *G16H 30/40* | (2018.01) | |
| *H04W 8/14* | (2009.01) | |
| *H04L 29/08* | (2006.01) | |
| *H04W 8/00* | (2009.01) | |
| *H04W 92/20* | (2009.01) | |
| *H04L 29/12* | (2006.01) | |
| *G06T 7/13* | (2017.01) | |
| *H04W 12/00* | (2021.01) | |
| *H04L 29/06* | (2006.01) | |
| *H04W 8/26* | (2009.01) | |
| *H04W 88/08* | (2009.01) | |

(52) U.S. Cl.
CPC .......... *G06T 11/008* (2013.01); *G16H 30/40* (2018.01); *H04L 61/2015* (2013.01); *H04L 61/256* (2013.01); *H04L 61/2592* (2013.01); *H04L 67/2814* (2013.01); *H04L 67/2857* (2013.01); *H04L 67/2895* (2013.01); *H04W 8/005* (2013.01); *H04W 92/20* (2013.01); *G06T 2207/10104* (2013.01); *G06T 2211/408* (2013.01); *G06T 2211/424* (2013.01); *H04L 63/164* (2013.01); *H04W 8/26* (2013.01); *H04W 12/001* (2019.01); *H04W 88/08* (2013.01)

(56) References Cited

U.S. PATENT DOCUMENTS

| | | | | |
|---|---|---|---|---|
| 8,750,587 | B2* | 6/2014 | Gagnon | G06T 11/006 |
| | | | | 382/131 |
| 8,767,908 | B2* | 7/2014 | Leahy | G06T 11/005 |
| | | | | 378/4 |
| 8,903,152 | B2* | 12/2014 | Asma | G06T 11/006 |
| | | | | 382/131 |
| 8,923,588 | B2* | 12/2014 | Laurence | G01T 1/2985 |
| | | | | 382/131 |
| 9,474,495 | B2* | 10/2016 | Ahn | A61B 6/4417 |
| 10,537,299 | B2* | 1/2020 | Wang | G21H 5/02 |
| 10,852,449 | B2* | 12/2020 | Panin | G06T 11/005 |
| 2011/0110571 | A1 | 5/2011 | Bar-Shalev | |
| 2012/0070050 | A1* | 3/2012 | Panin | G06T 11/005 |
| | | | | 382/131 |
| 2013/0094738 | A1 | 4/2013 | Bond | |
| 2013/0141098 | A1 | 6/2013 | Bao | |
| 2015/0193927 | A1 | 7/2015 | Wang | |
| 2018/0211419 | A1* | 7/2018 | Zhu | G06T 7/11 |
| 2019/0197674 | A1* | 6/2019 | Bai | G06T 11/008 |
| 2019/0346577 | A1* | 11/2019 | Bai | A61B 6/037 |

OTHER PUBLICATIONS

International Search Report and Written Opinion of PCT/EP2018/050013 dated Apr. 19, 2018.

* cited by examiner

USING TIME-OF-FLIGHT TO DETECT AND CORRECT MISALIGNMENT IN PET/CT IMAGING

Cross-Reference to Prior Applications

This application is the U.S. National Phase application under 35 U.S.C. §371 of International Application No. PCT/EP2018/050013, filed on Jan. 2, 2018, which claims the benefit of U.S. Provisional Patent Application No. 62/443,013, filed on Jan. 6, 2017. These applications are hereby incorporated by reference herein.

FIELD

The following relates generally to the medical imaging arts, positron emission tomography (PET) imaging and image reconstruction arts and related arts.

BACKGROUND

In positron emission tomography (PET) imaging, a radiopharmaceutical is administered to a patient, e.g. by intravascular infusion. The radiopharmaceutical may, for example, be a glucose-containing pharmaceutical agent such as fluorodeoxyglucose (FDG) in which the glucose molecules are tagged with a positron-emitting radioisotope such as fluorine-18 ($^{18}F$). The $^{18}F$-tagged glucose preferentially concentrates in high-metabolism tissue, so that the resulting PET image is a functional image representing a metabolic distribution. Each radioactive decay event detected in PET is produced by a sequence in which an emitted positron rapidly annihilates with an electron yielding two oppositely directed 511 keV gamma rays. The two 511 keV gamma rays are detected by two different PET detectors as substantially simultaneous events defining a line of response (LOR) connecting the two detections.

In conventional PET, the two 511 keV detection events are deemed to be simultaneous if they both occur within a specified narrow time window, and the counts which are reconstructed are detection counts along different LORs defined by various detector pairs. The resulting PET imaging data are reconstructed using an image reconstruction algorithm such as maximum likelihood expectation maximization (MLEM), ordered subset expectation maximization (OSEM), or the like. Various improvements on the base reconstruction are typically employed, most commonly including the use of an attenuation map, e.g. generated from a corresponding transmission computed tomography (CT) image, to compensate for absorption of some 511 keV rays in the imaged subject. Other known improvements include various scatter correction approaches, and/or the use of regularization via a prior to introduce a priori information into the reconstruction, and/or the use of a smoothing filter or the like.

In a variant approach, referred to as time-of-flight (TOF) PET, the location of the positron (or, more precisely, the positron-electron annihilation) producing each event is further localized along the LOR based on the small but finite time difference (or lack thereof) between the two detections. Intuitively, if the annihilation occurs midway between the two detectors then the time difference will be zero since both 511 keV gamma rays travel the same distance to the respective detectors. By contrast, if the annihilation occurs closer to one detector than the other, than the travel distances are different and the detector closest to the annihilation event will detect its 511 keV event first, followed very shortly thereafter (on the order of a nanosecond or less) by the second detection.

TOF PET requires radiation detectors with sufficiently high speed to resolve time differences on the order of a few hundred picoseconds, providing spatial localization along the LOR on the order of 10-20 centimeters or less. The TOF image reconstruction can employ the same improvements as conventional PET image reconstruction (e.g. using an attenuation map, scatter correction, et cetera) and the better spatial localization of the detected counts via TOF localization reduces noise and other artifacts. Consequently, if a PET imaging data acquisition system has sufficiently fast radiation detectors, it is usually used to acquire PET imaging data having TOF localization, and a TOF image reconstruction is employed to generate the reconstructed image.

The following discloses a new and improved systems and methods.

SUMMARY

In one disclosed aspect, a positron emission tomography (PET) image reconstruction device is disclosed, including an electronic processor and a non-transitory storage medium storing instructions readable and executable by the electronic processor to reconstruct PET imaging data having TOF localization by operations including: performing a TOF image reconstruction on the PET imaging data to produce a TOF reconstructed image wherein the TOF image reconstruction utilizes the TOF localization of the PET imaging data; performing a non-TOF image reconstruction on the PET imaging data to produce a non-TOF reconstructed image wherein the non-TOF image reconstruction does not utilize the TOF localization of the PET imaging data; computing a comparison image indicative of differences between the TOF reconstructed image and the non TOF reconstructed image; determining an adjustment for the TOF image reconstruction based on the comparison image; and performing the TOF image reconstruction on the PET imaging data with the determined adjustment to produce an adjusted TOF reconstructed image.

In another disclosed aspect, a non-transitory storage medium stores instructions readable and executable by an electronic processor to process PET imaging data having TOF localization by processing operations comprising: performing a TOF image reconstruction on the PET imaging data to produce a TOF reconstructed image wherein the TOF image reconstruction utilizes the TOF localization of the PET imaging data and includes attenuation correction using an attenuation map; performing a non-TOF image reconstruction on the PET imaging data to produce a non-TOF reconstructed image wherein the non-TOF image reconstruction does not utilize the TOF localization of the PET imaging data and includes attenuation correction using the attenuation map; computing a comparison image indicative of differences between the TOF reconstructed image and the non-TOF reconstructed image; and identifying an error in the TOF reconstructed image using the comparison image.

In another disclosed aspect, a method of processing PET imaging data having TOF localization is disclosed. The method comprises: performing a TOF image reconstruction on the PET imaging data to produce a TOF reconstructed image wherein the TOF image reconstruction utilizes the TOF localization of the PET imaging data and includes attenuation correction using an attenuation map; performing a non-TOF image reconstruction on the PET imaging data to produce a non-TOF reconstructed image wherein the non- TOF image reconstruction does not utilize the TOF localization of the PET imaging data and includes attenuation correction using the attenuation map; and identifying an error in the TOF reconstructed image based on a comparison of the TOF reconstructed image and the non-TOF reconstructed image. The error may be displayed on a display, and/or the error may be corrected and the TOF image reconstruction repeated to produce an improved TOF reconstructed image. The TOF image reconstruction, the non-TOF image reconstruction, and the identifying are suitably performed by an electronic processor.

One advantage resides in providing improved PET image quality and quantitative accuracy.

Another advantage resides in detecting spatial misalignment of the attenuation map used in PET image reconstruction respective to the PET imaging data.

Another advantage resides in detecting the direction of spatial misalignment of the attenuation map used in PET image reconstruction respective to the PET imaging data.

Another advantage resides in detecting the magnitude of spatial misalignment of the attenuation map used in PET image reconstruction respective to the PET imaging data.

Another advantage resides in providing for correction of spatial misalignment of the attenuation map used in PET image reconstruction respective to the PET imaging data.

Another advantage resides in detecting errors in scatter correction used in PET image reconstruction.

Another advantage resides in providing for correction of errors in scatter correction used in PET image reconstruction.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Geometric misalignment between PET imaging data and the attenuation map used in reconstructing the PET imaging data is a known problem. It is partially addressed in many imaging laboratories by the use of a combined or "hybrid" imaging system that includes both a PET imaging data acquisition gantry and a CT imaging data acquisition gantry, along with a common patient table for transporting the patient into the CT gantry for CT imaging and into the PET gantry for PET imaging. In this way, the common patient table provides a common frame of reference for the PET imaging data and the attenuation map generated from the CT image. However, the spatial alignment between the PET imaging data and the attenuation map should ideally be accurate to within the resolution of the PET image, and this level of alignment precision is usually not obtained by use of a hybrid PET/CT imaging system in the presence of patient motion. Alignment can also be achieved using spatial registration processing to spatially register the PET and CT images; however, spatial registration is made less accurate by the fundamentally different contrast mechanisms in PET and CT which makes identification of usable spatial landmarks difficult. Moreover, the PET image used for the spatial registration is usually itself not attenuation-corrected, which can degrade the PET image and thereby compromise the subsequent CT image spatial registration.

Attenuation map misalignment can introduce artifacts in the reconstructed PET image, such as band artifacts in lung/soft tissue boundaries, ghost lesions, and quantitative bias such as erroneous tumor SUV values, and so forth. In clinical applications, physicians usually perform visual inspection to check if PET/CT misalignment is present in the patient studies, using fused PET/CT images, for example, but this approach can fail to detect misalignment sufficient to generate clinically significant artifacts.

Time-of-flight (TOF) PET provides TOF localization for the counts making up the PET imaging data. The TOF localization used in iterative TOF image reconstruction improves the resulting TOF reconstructed PET image quality by incorporating the TOF information into the reconstruction models. The TOF localization provides an effective sensitivity gain for the PET images, which provides practical benefits such as faster PET scans and/or reduced radiopharmaceutical dose, improved small lesion detection, reduced quantitative bias, and so forth. In view of this, non-TOF image reconstruction is usually not employed where the PET imaging data to be reconstructed includes TOF localization.

However, it is recognized herein that comparison of the TOF reconstructed image with a non-TOF reconstructed image produced by a non-TOF image reconstruction that does not utilize the TOF localization can provide useful information for detecting errors in the TOF reconstruction. For example, misalignment between the PET imaging data and the attenuation map can be easily detected, including in some cases the direction and magnitude of the misalignment, and can then be corrected to improve the TOF reconstructed image.

More generally, other sources of PET imaging data/attenuation map misalignment can be identified. In clinical studies, such misalignment can be due to diverse sources such as incorrectly completed alignment calibration, patient table bending or deflection (which can also be weight dependent), patient motion (voluntary or involuntary), tissue and/or CT contrast agent redistribution, and so forth. As the PET imaging relies on the attenuation map, usually derived from CT, to correct for attenuation, any misalignment between PET and CT images can adversely affect and bias the reconstructed activity distribution in PET images. Similar issues arise in scatter correction.

In approaches disclosed herein, separate TOF and non-TOF reconstructed images are generated, and comparison of these images enables detection of misalignment of the attenuation map respective to the PET imaging data. Optionally, the misalignment is automatically corrected, or may be semi-automatically corrected using iterative detection and realignment. The disclosed approaches are based on the insight that the TOF reconstructed image has reduced artifacts due to the attenuation map misalignment as compared to the non-TOF reconstructed image.

Without being limited to any particular theory of operation, the difference between TOF and non-TOF in susceptibility to attenuation map misalignment artifacts is believed to be due to improved spatial localization provided by the TOF localization. A misalignment of the attenuation map tends to bias the reconstructed intensity in a particular pattern associated with the specific misalignment. In the case of a non-TOF image reconstruction, the intrinsic counts are only localized to a LOR, and hence the annihilation event corresponding to a count can (in a conceptual sense) be slid anywhere along the LOR, so as to (erroneously) accommodate the misalignment of the attenuation map. By contrast, in the case of a TOF image reconstruction, the intrinsic counts are further localized along the LOR in accord with the TOF localization, and hence the annihilation event corresponding to a count is further constrained to a portion of the LOR, thereby reducing the potential to (erroneously) accommodate the misalignment of the attenuation map by sliding the annihilation event along the LOR.

Figure 1:
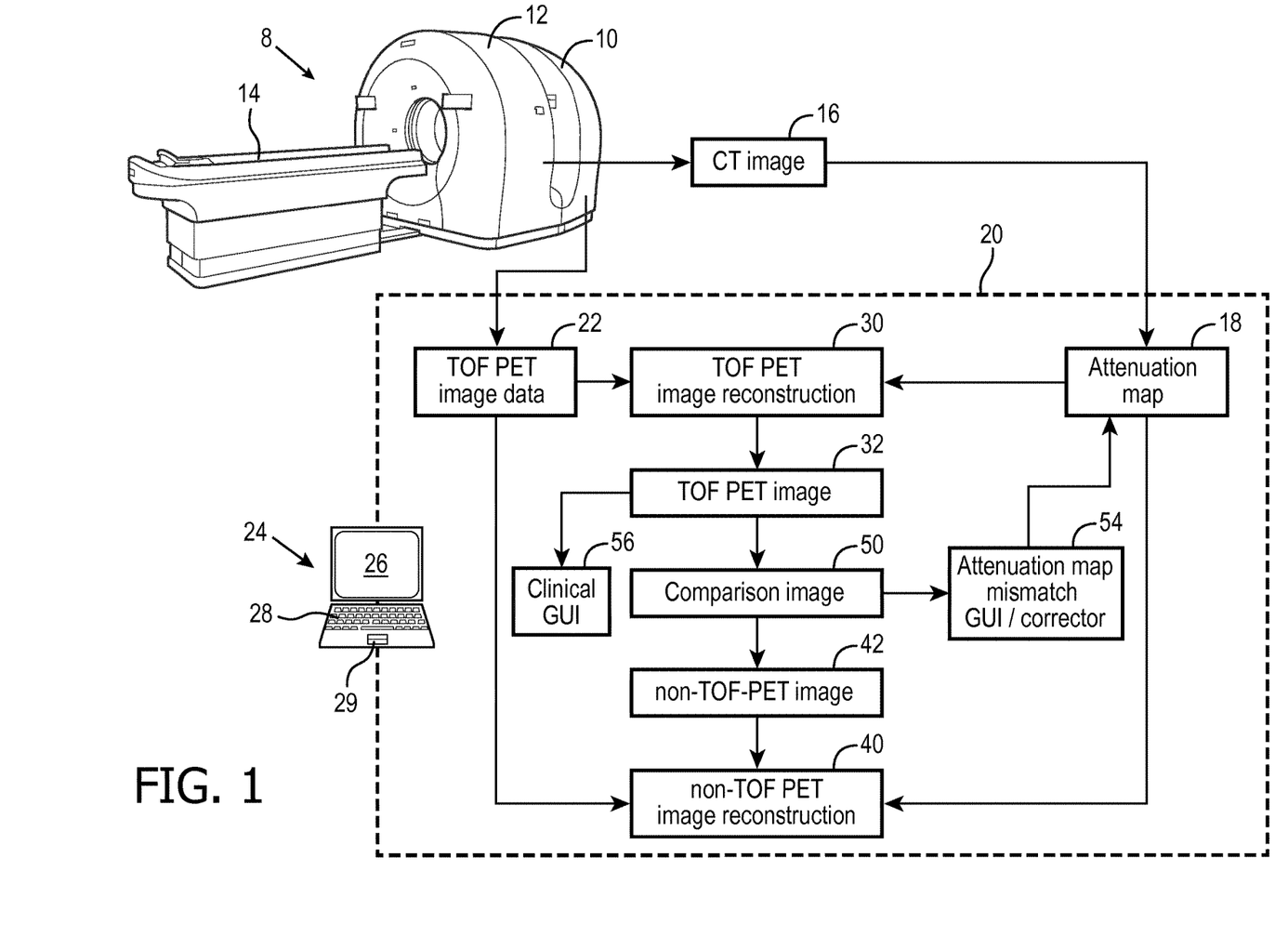
FIG. 1 diagrammatically illustrates a positron emission tomography (PET) imaging system.

With reference to FIG. 1, an illustrative imaging system is a combined positron emission tomography (PET)/transmission computed tomography (CT) imaging device 8, which includes both a PET imaging gantry or scanner 10 and a CT gantry or scanner 12 mounted with coaxial bores such that a patient may be loaded onto a common patient table 14 and loaded into either the CT gantry 12 for CT imaging or the PET gantry 10 for PET imaging. The PET imaging gantry or scanner 10 has radiation detectors which are fast enough to provide TOF localization of counts along the lines of response (LORs). For example, in some non-limiting examples the detectors may have 640 picosecond temporal resolution, or in embodiments with better TOF resolution the detectors may have 320 picosecond temporal resolution. By way of non-limiting illustrative example, the illustrative PET/CT imaging device imaging scanner 6 may be the PET gantry of a Vereos™ Digital PET/CT scanner, available from Koninklijke Philips N.V., Eindhoven, the Netherlands. An advantage of employing the combined PET/CT imaging device 8 for the PET imaging study is that the CT scanner 12 can be used to acquire a CT image 16 that is converted to an attenuation map 18 by appropriate conversion of the Hounsfield numbers of the CT image to corresponding absorption values at 511 keV (the energy of gamma rays emitted during positron-electron annihilation events). In other contemplated embodiments the imaging scanner may be a hybrid PET/magnetic resonance (MR) imaging device, in which case the attenuation map 18 may be generated from an MR image using suitable substitution of known attenuation values for 511 keV radiation in various organs and tissues identified in the MR image by manual, automated, or semi-automated image segmentation.

As diagrammatically shown in FIG. 1, an electronic processor 20 processes PET imaging data 22 acquired by the PET imaging gantry or scanner 10 to generate a reconstructed PET image. The electronic processor 20 may, for example, be embodied as a computer 24 (e.g. a desktop computer, network-based server computer, a dedicated PET control computer, various combinations thereof, or so forth) that executes instructions read from one or more non-transitory storage media (e.g. one or more hard drives, optical disks, solid state drives or other electronic digital storage devices, various combinations thereof, or so forth) that stores the instructions. The computer 24 typically includes or has operative access to at least one display 26 (e.g. an LCD display, plasma display, or so forth) for displaying reconstructed PET (and optionally CT) images, and optionally also including one or more user input devices such as an illustrative keyboard 28, an illustrative trackpad 29 (or mouse, trackball, touch-sensitive overlay of the display 26, or other pointing device), or so forth.

The electronic processor 20 performs a TOF image reconstruction 30 (e.g., MLEM, OSEM, or so forth, optionally including regularization using a relative difference penalty prior, quadratic prior, or so forth) on the PET imaging data 22 to produce a TOF reconstructed image 32. The TOF image reconstruction 30 utilizes the TOF localization of the PET imaging data 22. The illustrative TOF image reconstruction 30 also includes attenuation correction using the attenuation map 18. The TOF image reconstruction 30 may also perform scatter correction, e.g. using convolution-subtraction scatter correction, Monte Carlo scatter modeling, employing a Gaussian fit to the scatter, or so forth.

Additionally, the electronic processor 20 performs non-TOF image reconstruction 40 on the PET imaging data 22 to produce a non-TOF reconstructed image 42. The non-TOF image reconstruction 40 does not utilize the TOF localization of the PET imaging data 22, but the illustrative non-TOF image reconstruction 40 does also include attenuation correction using the attenuation map 18. The same attenuation map 18 is used for both the TOF image reconstruction 30 and the non-TOF image reconstruction 40. However, as discussed elsewhere herein, the effective sensitivity gain provided by the TOF image reconstruction 30 compared with the non-TOF image reconstruction 40 makes the former more robust against artifacts due to spatial misalignment of the attenuation map 18 (e.g. a spatial shift of the attenuation map 18, and/or a spatial rotation of the attenuation map 18) respective to the PET imaging data 22.

Accordingly, a comparison image 50 is computed, which is indicative of differences between the TOF reconstructed image 32 and the non-TOF reconstructed image 42. The comparison image 50 may be computed using any comparative computation that provides comparison image intensity that reflects the difference between the two images 32, 42. In illustrative examples herein, the comparison image 50 is computed on a per-voxel (or more generally, per-image element) basis according to the squared difference $(R1-R2)^2$ where R1 is the voxel value for the TOF reconstructed image 32 and R2 is the voxel value for the non-TOF reconstructed image 42. Other difference metrics besides this illustrative squared difference $(R1-R2)^2$ may be employed, such as an absolute value difference $|R1-R2|$.

In an adjustment operation or tool 54, an adjustment is determined for the TOF image reconstruction 30 based on the comparison image 50. For example, in some embodiments the adjustment includes a spatial correction for the attenuation map 18, e.g. a spatial shift and/or spatial rotation to account for a misalignment of the attenuation map 18 respective to the PET imaging data 22 as indicated by the comparison image 50.

In other embodiments, the adjustment entails replacing a portion of the attenuation map 18 corresponding to a difference identified in the comparison image 50 with an attenuation correction derived from the PET imaging data 22, e.g. estimated from a reconstructed PET image generated using the TOF image reconstruction 30 but without attenuation correction. This approach is suitable where there is reason to conclude that the subject region of the attenuation map 18 is unreliable, e.g. due to patient motion or CT contrast redistribution during the scans.

In other embodiments, the adjustment may entail an adjustment of the scatter correction employed in the TOF image reconstruction 30. In general, scatter correction errors are expected to manifest in the comparison image 50 as relatively symmetric, large-area and low intensity regions, whereas artifacts due to misalignment of the attenuation map 18 are expected to manifest as higher intensity spatially discrete regions, typically in the form of a broadened outline of an image feature in the comparison image 50.

The adjustment operation or tool 54 can take various forms. In one embodiment, the direction of the spatial misalignment of the attenuation map 18 respective to the PET imaging data 22 is determined based on position of the detected broadened outline relative to the image feature, and the magnitude of that spatial misalignment is determined based on a breadth of the broadened outline. On this basis, the operation 54 can automatically adjust the attenuation map 18 by imposing a rigid shift or rotation to compensate for the thusly determined direction and magnitude of the attenuation map misalignment.

In other embodiments, the adjustment operation or tool 54 comprises a graphical user interface (GUI) displayed on the display 26 which shows the comparison image 50 and allows a user operating the user input device(s) 28, 29 to input the appropriate adjustment, for example by clicking on the broadened outline and using GUI rulers to mark the location and width of the broadened outline and the feature, from which information the electronic processor 20 can compute the adjustment. In the case of an adjustment in which a portion of the attenuation map 18 is replaced with an attenuation correction derived from the PET imaging data 22, the user may suitably draw a contour indicating the region to be replaced. In the case of a scatter correction adjustment, the user may operate a slider or other GUI input to adjust a parameter of the scatter correction. These are merely illustrative examples of embodiments of the adjustment operation or tool 54.

With the adjustment determined, the TOF image reconstruction 30 is again performed (i.e. repeated) on the PET imaging data 22 with the determined adjustment (e.g., the shifted or rotated attenuation map 18) to produce an adjusted TOF reconstructed image (replacing the TOF image 32). In some embodiments, this process is repeated one or more times, i.e. the non-TOF image 42 is also re-computed with the same adjustment and the comparison image 50 recalculated, and such process may be iterated one or more times until the comparison image 50 no longer indicates spatial misalignment of the attenuation map 18 or other identifiable error in the TOF image reconstruction 30. The final TOF reconstructed image 32 is then output as the final clinical image to be shown on the display 26 via a suitable clinical GUI 56 which optionally may, for example, include conversion of the final image to standardized uptake value (SUV) units, provide the ability to zoom, pan, or otherwise manipulate the displayed image, or so forth.

In disclosed approaches, comparison of the TOF reconstructed image 32 and the non-TOF reconstructed image 42 provides for detecting misalignment of the attenuation map 18 automatically. Optionally, the attenuation map is automatically corrected (i.e. realigned), or semi-automatically corrected using iterative detection and realignment. In general, the disclosed approaches are based on the insight that the TOF image 32 has reduced misalignment artifacts as compared to non-TOF image 42 (or TOF image with lower TOF resolution). The TOF localization is exploited for this purpose, which helps for more appropriate placement of the reconstructed activity despite the errors introduced by misaligned attenuation map.

Figure 2:
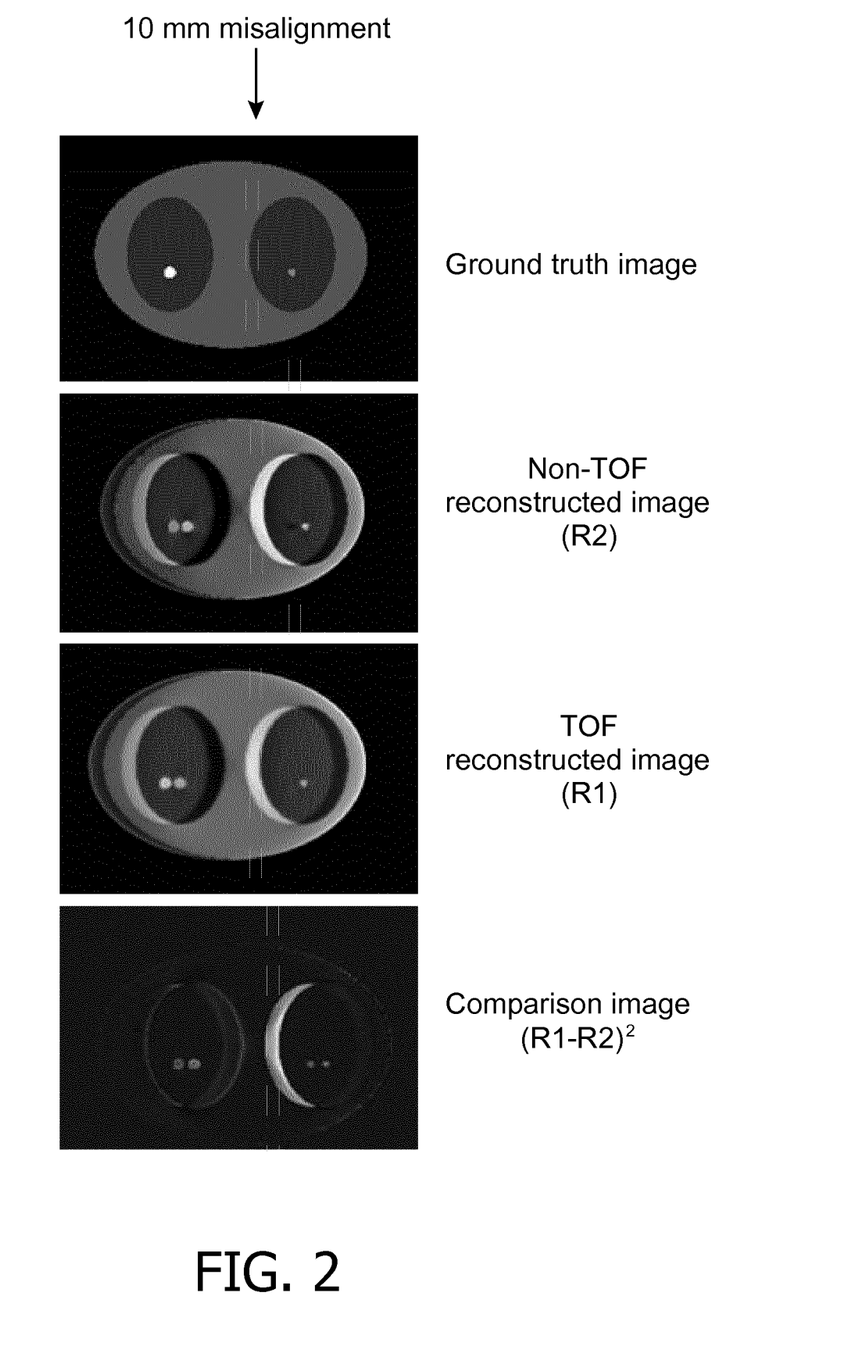
FIGS. 2, 5, and 6 illustrate phantom PET imaging simulation results as described herein.
Figure 3:
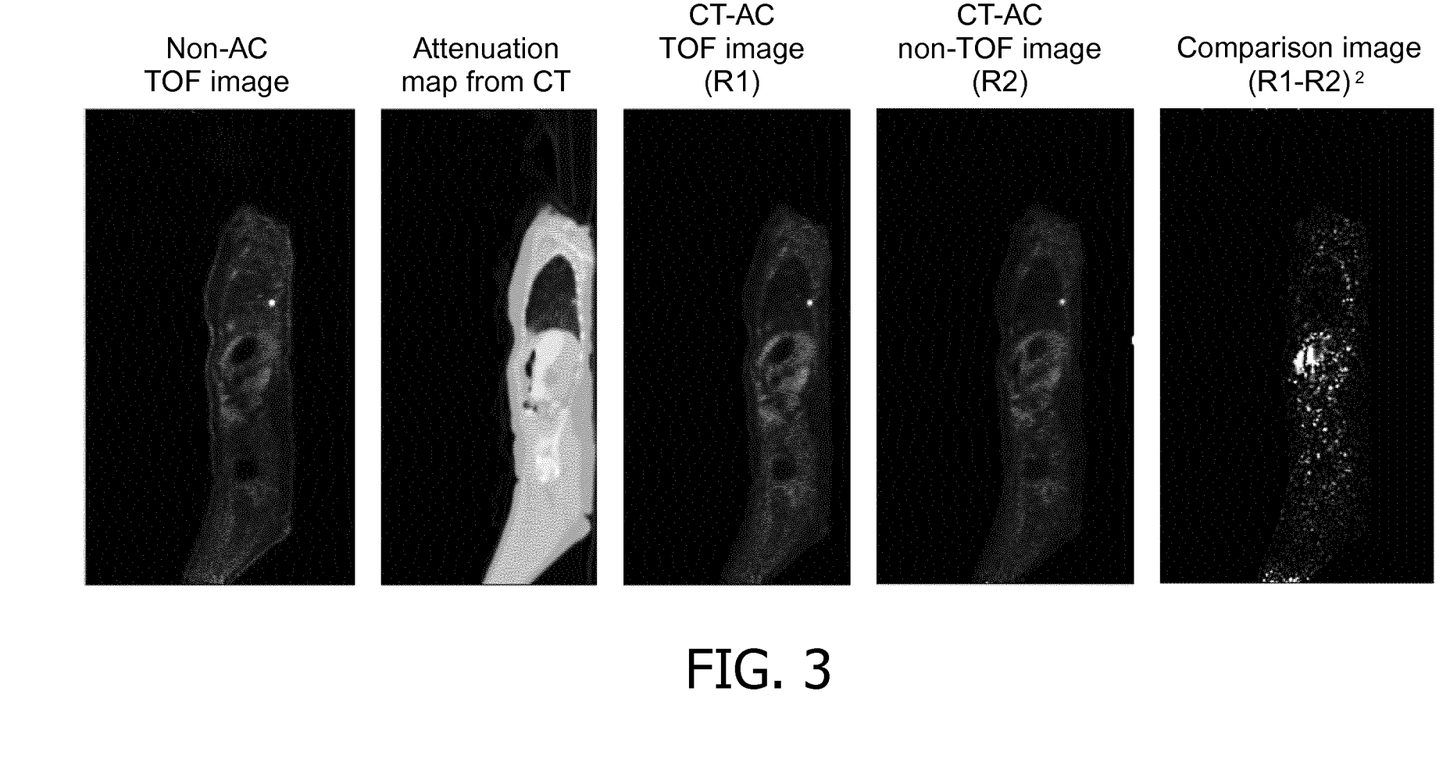
FIGS. 3 and 4 illustrate clinical PET imaging results as described herein.
Figure 4:
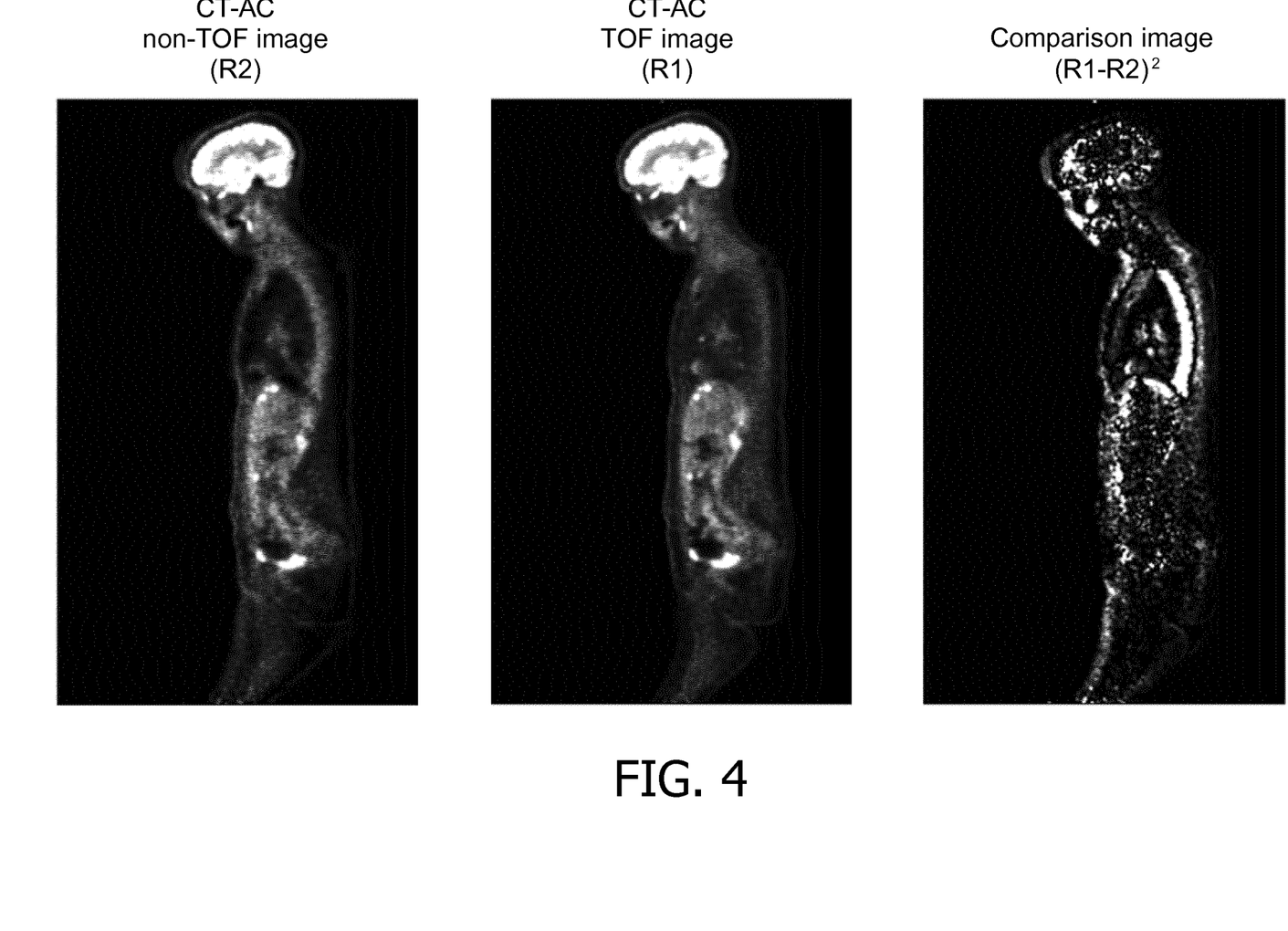

With reference to FIGS. 2-6, various aspects of the foregoing disclosure are further illustrated by examples produced by simulated phantom PET imaging (FIGS. 2, 5, and 6) and actual medical imaging of human subjects (FIGS. 3 and 4). In these examples, for detection of PET/CT misalignment, the comparison image 50 is computed using the squared difference of R1 and R2, i.e. $(R1-R2)^2$. As the attenuation map 18 in these illustrative examples is derived from the CT image 16, the misalignment is also sometimes referred to herein loosely as PET/CT misalignment.

With reference now to FIG. 2, results of a phantom PET imaging simulation study are presented, for data with 320 ps TOF resolution. The uppermost image shows the "ground truth image", i.e. the actual phantom. The image labeled "TOF reconstructed image (R1)" corresponds to TOF reconstructed image 32 of FIG. 1. The image labeled "Non-TOF reconstructed image (R2)" corresponds to the non-TOF reconstructed image 42 of FIG. 1. In this simulation, a 10 mm PET/CT misalignment was introduced. The bottommost image of FIG. 2 is the squared difference image, $(R1-R2)^2$ corresponding to the comparison image 50 of FIG. 1. The comparison image shows a broadened outline, i.e. a strong band (moon shape) is observed, indicating the CT image is misaligned with PET image in a way that the CT image is moved to "patient" (i.e. the phantom) left (so the mediastinum of CT is overlaid with lung in PET) where the broadened outline is positioned. The TOF image R1 shows reduced misalignment artifacts as compared with the non-TOF image R2. The squared difference image, $(R1-R2)^2$ shows a strong band, i.e. broadened outline, where soft tissue (here mediastinum) in CT overlays in the lung of the PET image. Ghost images also are apparent, which show as bright spots in the $(R1-R2)^2$ image.

With reference to FIG. 3, results of a patient study are shown, in which the PET imaging data were acquired with 325 ps TOF resolution. In FIG. 3 the images are, from left to right: non-attenuation corrected (NAC) TOF image; CT map used for attenuation correction (CT-AC); TOF image with CT-AC (R1); non-TOF image with CT-AC (R2); and the comparison image $(R1-R2)^2$. Strong bands in the stomach region (that is, broadened outlines of the stomach feature) are seen in the comparison image, which are indicative of PET/CT misalignment. By way of analysis of the images and the clinical workflow, it was determined that this PET/CT misalignment was introduced by redistribution between CT and PET scans of a contrast agent that was administered for the CT imaging.

With reference to FIG. 4, results of a patient study are shown, in which the PET imaging data were acquired with 325 ps TOF resolution, and with an introduced 20 mm PET/CT misalignment. In FIG. 4 the images are, from left to right: the CT-AC non-TOF image (R2); the CT-AC TOF image (R1); and the comparison image $(R1-R2)^2$. The band in the comparison image corresponds to a broadened outline of the thoracic cavity, and indicates misalignment of CT with PET in which the CT was moved up from back to chest. The thickness of this band is about 20 mm, consistent with the true introduced misalignment.

Figure 5:
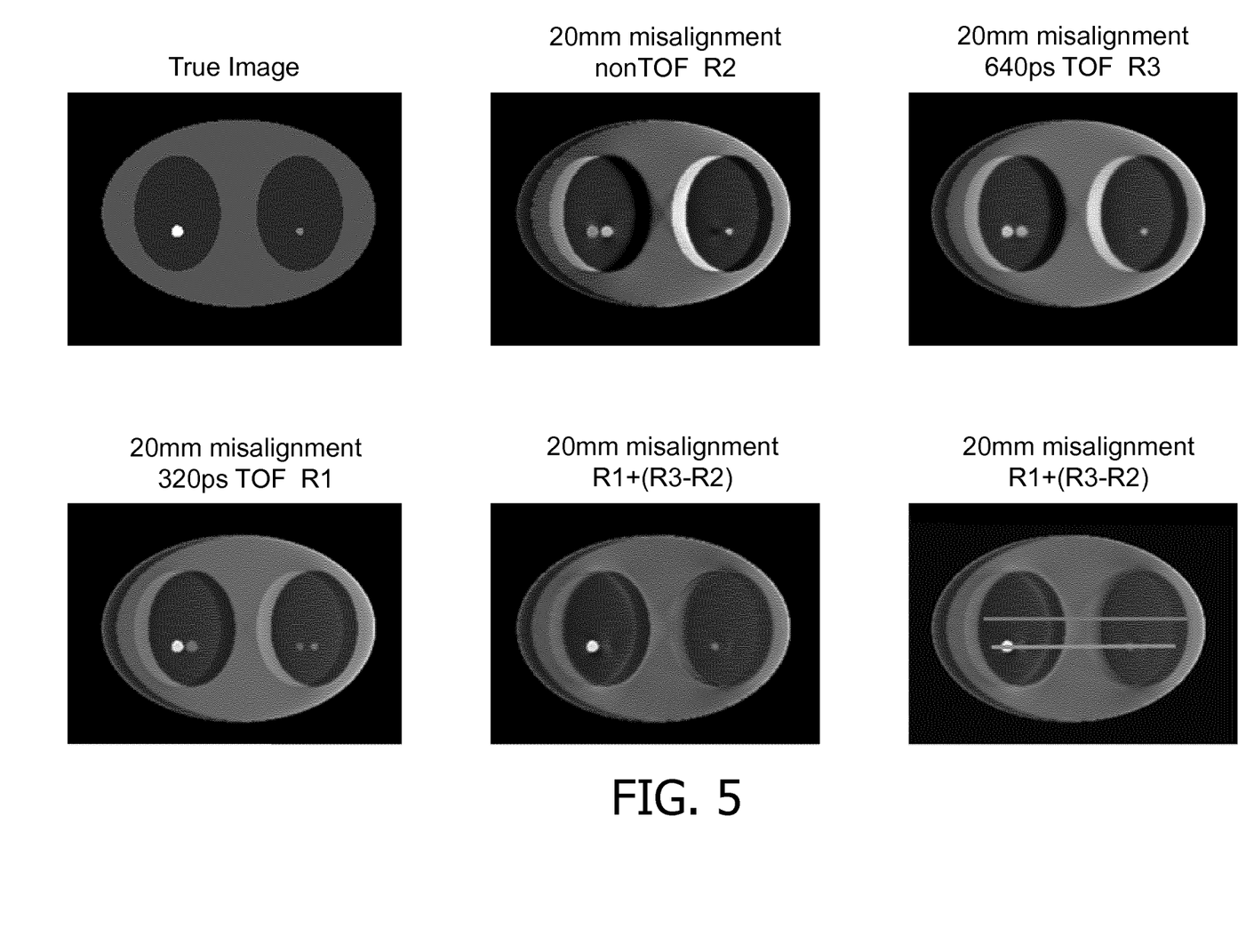
Figure 6:
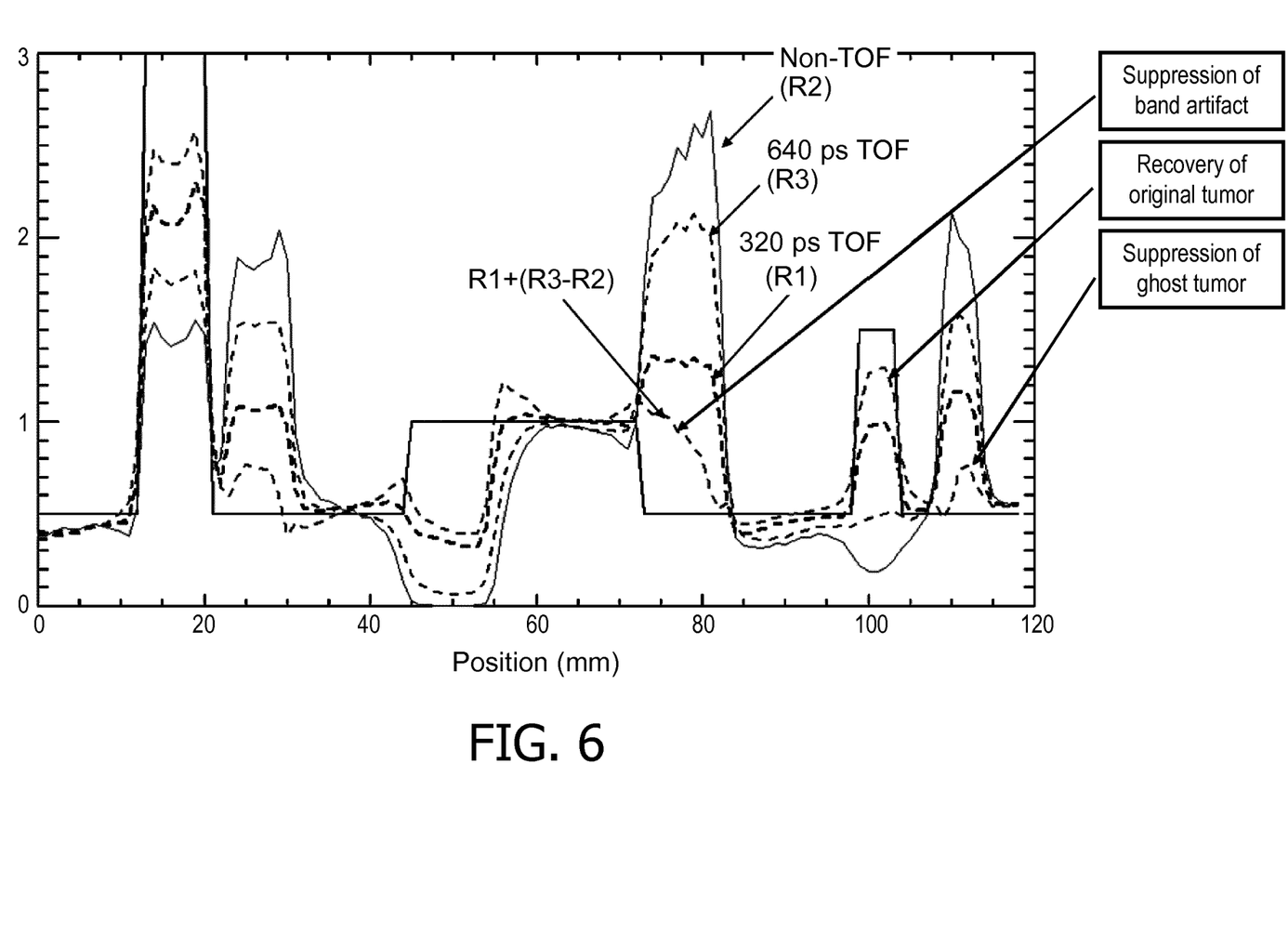

With reference to FIGS. 5 and 6, results are presented for a phantom PET imaging simulation study with 320 ps TOF resolution. A 20 mm misalignment between PET and CT was introduced. In FIG. 5, the images are, top row left-to-right: the ground truth phantom image; a non-TOF reconstructed image (R2); and a TOF reconstructed image with TOF resolution of 640 ps (R3). The images on the bottom row are, from left-to-right: a TOF reconstructed image with TOF resolution of 320 ps (R1); an image computed from the images R1, R2, and R3 according to the formula R1+(R3−R2); and the same image computed according to the formula R1+(R3−R2) with line profiles indicated. FIG. 6 plots the line profiles indicated in the bottom rightmost image of FIG. 5.

The image R3 is a low TOF resolution image (LresTOF), reconstructed from the same data but assuming the TOF resolution is lower than the true TOF resolution of the data. R3 reconstruction (1) intentionally degrades the TOF resolution of the data using a calculated Gaussian kernel and (2) models the lowered TOF resolution in the iterative reconstruction. A misalignment correction can be obtained using the linear combination of R1, R2, and R3, e.g., corrected image R1+(R3−R2). The image computed as R1+(R3−R2) showed near perfect removal of the ghost tumors, significant reduction of the band artifact, and improved tumor recovery. Other correction approaches can be designed to iteratively detect misalignment and realign PET and CT images until a minimal misalignment is detected.

In this example, the R1 (320 ps TOF) image showed least artifacts, but still showed the ghost tumors. The R2 image (non-TOF) showed strongest artifacts. The R3 image (640 ps TOF) had artifact levels between those of R1 and R2. The corrected image R1+(R3−R2) showed much reduced artifacts and the ghost tumors are nearly gone. Line profiles shown in FIG. 6 along the profile lines shown in the bottom rightmost image of FIG. 5 indicate near perfect removal of the ghost tumors and much improved tumor quantitation using the simple linear image combination R1+(R3−R2).

More generally, for optimized performance of misalignment compensation in CTAC images, different image combinations can be used. Also different R3 image can be used. In the simulation of FIGS. 5 and 6 with 320 ps TOF resolution, the intermediate 640 ps TOF resolution was chosen to reconstruct R3. For different systems with different TOF resolution, different TOF resolution for R3 image reconstruction can be used. The results show that if the original TOF resolution of the data is not high, e.g., if the TOF is 640 ps in the original data, the correction will be less effective since the difference between 640 ps TOF image and non-TOF image is less significant to effectively correct for the misalignment. In this illustrative example, for misalignment correction is completely automatic. Another way of using TOF for misalignment correct can be applied to the CT image directly using an iterative approach of misalignment detection and CT realignment to PET till the residual misalignment is acceptable. The final realigned CT image can then be used for attenuation and scatter correction. This approach may need user interaction to determine the misalignment and invoke realignment, thus is semi-automatic. If certain severe misalignment regions can be detected, then TOF maximum likelihood derivation of attenuation and activity (TOF-MLAA approach) can be utilized for those regions.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A positron emission tomography (PET) image reconstruction device comprising:
an electronic processor; and
a non-transitory storage medium storing instructions readable and executable by the electronic processor to reconstruct PET imaging data having TOF localization by operations including:
performing a TOF image reconstruction on the PET imaging data to produce a TOF reconstructed image wherein the TOF image reconstruction utilizes the TOF localization of the PET imaging data;
performing a non-TOF image reconstruction on the PET imaging data to produce a non-TOF reconstructed image wherein the non-TOF image reconstruction does not utilize the TOF localization of the PET imaging data;
computing a comparison image indicative of differences between the TOF reconstructed image and the non-TOF reconstructed image;
determining an adjustment for the TOF image reconstruction based on the comparison image; and
performing the TOF image reconstruction on the PET imaging data with the determined adjustment to produce an adjusted TOF reconstructed image.

2. The PET image reconstruction device of claim 1 wherein the TOF image reconstruction employs an attenuation map, the non-TOF image reconstruction employs the attenuation map, and the adjustment comprises a spatial adjustment of the attenuation map including at least one of a spatial shift of the attenuation map and a spatial rotation of the attenuation map.

3. The PET image reconstruction device of claim 2 wherein the determining of the spatial adjustment of the attenuation map includes:
detecting a broadened outline of an image feature in the comparison image; and
determining the spatial adjustment based on the detected broadened outline.

4. The PET image reconstruction device of claim 1 wherein the TOF image reconstruction employs an attenuation map, the non-TOF image reconstruction employs the attenuation map, and the adjustment comprises replacing a portion of the attenuation map corresponding to a difference identified in the comparison image with an attenuation correction derived from the PET imaging data.

5. The PET image reconstruction device of claim 1 wherein:
the performing of TOF image reconstruction on the PET imaging data includes performing a TOF image reconstruction on a portion of the PET imaging data having high resolution TOF localization to produce a high resolution TOF reconstructed image and performing a TOF image reconstruction on a portion of the PET imaging data having coarse resolution TOF localization to produce a coarse resolution TOF reconstructed image; and
computing the comparison image includes computing an image R1+(R3−R2) wherein R2 denotes the non-TOF reconstructed image.

6. The PET image reconstruction device of claim 1 further comprising:
a display; and
at least one user input device;
wherein the determining of the adjustment for the TOF image reconstruction (30) includes displaying the comparison image on the display and receiving the adjustment via the at least one user input device.

7. A positron emission tomography (PET) imaging device comprising:
a time of flight (TOF) PET imaging data acquisition device configured to acquire PET imaging data having TOF localization;
a PET image reconstruction device as set forth in claim 1; and a display operatively connected with the PET image reconstruction device to display the adjusted TOF reconstructed image.

8. A non-transitory storage medium storing instructions readable and executable by an electronic processor to process positron emission tomography (PET) imaging data having time of flight (TOF) localization by processing operations comprising:
- performing a TOF image reconstruction on the PET imaging data to produce a TOF reconstructed image wherein the TOF image reconstruction utilizes the TOF localization of the PET imaging data and includes attenuation correction using an attenuation map;
- performing a non-TOF image reconstruction on the PET imaging data to produce a non-TOF reconstructed image wherein the non-TOF image reconstruction does not utilize the TOF localization of the PET imaging data and includes attenuation correction using the attenuation map;
- computing a comparison image indicative of differences between the TOF reconstructed image and the non-TOF reconstructed image; and
- identifying an error in the TOF reconstructed image using the comparison image.

9. The non-transitory storage medium of claim 8 wherein the identified error includes a spatial misalignment of the attenuation map respective to the PET imaging data.

10. The non-transitory storage medium of claim 8 wherein the identifying includes:
- detecting a broadened outline of an image feature in the comparison image; and
- identifying a spatial misalignment of the attenuation map respective to the PET imaging data based on the detected broadened outline.

11. The non-transitory storage medium of claim 10 wherein the identifying further includes identifying a direction of the spatial misalignment of the attenuation map respective to the PET imaging data based on position of the detected broadened outline relative to the image feature.

12. The non-transitory storage medium of claim 10 wherein the identifying further includes identifying a magnitude of the spatial misalignment of the attenuation map respective to the PET imaging data based on a breadth of the detected broadened outline.

13. The non-transitory storage medium of claim 9 wherein the processing operations further include:
- correcting the identified spatial misalignment of the attenuation map to generate a corrected attenuation map; and
- repeating the TOF image reconstruction including attenuation correction using the corrected attenuation map to produce an improved TOF reconstructed image.

14. The non-transitory storage medium of claim 8 wherein:
- the performing of TOF image reconstruction on the PET imaging data includes performing a TOF image reconstruction on a portion of the PET imaging data having high resolution TOF localization to produce a high resolution TOF reconstructed image and performing a TOF image reconstruction on a portion of the PET imaging data having coarse resolution TOF localization to produce a coarse resolution TOF reconstructed image; and
- computing the comparison image includes computing an image combining the high resolution TOF reconstructed image, the non-TOF reconstructed image, and the coarse resolution TOF reconstructed image.

15. A method of processing positron emission tomography (PET) imaging data having time of flight (TOF) localization, the method comprising:
- performing a TOF image reconstruction on the PET imaging data to produce a TOF reconstructed image wherein the TOF image reconstruction utilizes the TOF localization of the PET imaging data and includes attenuation correction using an attenuation map;
- performing a non-TOF image reconstruction on the PET imaging data to produce a non-TOF reconstructed image wherein the non-TOF image reconstruction does not utilize the TOF localization of the PET imaging data and includes attenuation correction using the attenuation map;
- identifying an error in the TOF reconstructed image based on a comparison of the TOF reconstructed image and the non-TOF reconstructed image; and
- at least one of (i) displaying the error on a display and (ii) correcting the error and repeating the TOF image reconstruction to produce an improved TOF reconstructed image;
- wherein the TOF image reconstruction, the non-TOF image reconstruction, and the identifying are performed by an electronic processor.

16. The method of claim 15 wherein the identifying comprises identifying a spatial misalignment of the attenuation map respective to the PET imaging data.

17. The method of claim 16 wherein the identifying includes:
- computing a comparison image indicative of differences between the TOF reconstructed image and the non-TOF reconstructed image;
- detecting a broadened outline of an image feature in the comparison image; and
- identifying the spatial adjustment based on the detected broadened outline.

18. The method of claim 17 wherein the identifying further includes identifying a direction of the spatial misalignment of the attenuation map respective to the PET imaging data based on position of the detected broadened outline relative to the image feature.

19. The method of claim 17 wherein the identifying further includes identifying a magnitude of the spatial misalignment of the attenuation map respective to the PET imaging data based on a breadth of the detected broadened outline.

20. The method of claim 16 wherein the displaying or correcting includes repeating the TOF image reconstruction with the attenuation map corrected for the identified spatial misalignment to generate an improved TOF reconstructed image.

* * * * *